United States Patent
Bernhardt et al.

(10) Patent No.: US 9,263,163 B2
(45) Date of Patent: Feb. 16, 2016

(54) ADAPTIVE X-RAY FILTER

(71) Applicants: Philipp Bernhardt, Forchheim (DE); Hans Liegl, Erlangen (DE); Reiner Franz Schulz, Erlangen (DE)

(72) Inventors: Philipp Bernhardt, Forchheim (DE); Hans Liegl, Erlangen (DE); Reiner Franz Schulz, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 299 days.

(21) Appl. No.: 13/875,988

(22) Filed: May 2, 2013

(65) Prior Publication Data

US 2013/0301807 A1  Nov. 14, 2013

(30) Foreign Application Priority Data

May 8, 2012  (DE) .................. 10 2012 207 627

(51) Int. Cl.
*G21K 1/10* (2006.01)
*A61B 6/00* (2006.01)

(52) U.S. Cl.
CPC ............... *G21K 1/10* (2013.01); *A61B 6/4035* (2013.01)

(58) Field of Classification Search
CPC ............................. A61B 6/4035; G21K 1/10
USPC .................................. 378/156–159
See application file for complete search history.

(56) References Cited

U.S. PATENT DOCUMENTS

| | | | | |
|---|---|---|---|---|
| 3,755,672 A * | 8/1973 | Edholm et al. | ................. | 378/158 |
| 4,772,407 A * | 9/1988 | Carlson | ............................. | 252/74 |
| 5,242,372 A * | 9/1993 | Carol | ................................ | 600/1 |
| 5,559,853 A * | 9/1996 | Linders et al. | ................. | 378/159 |
| 5,625,665 A * | 4/1997 | Fokkink et al. | ................ | 378/156 |
| 5,666,396 A * | 9/1997 | Linders et al. | ................. | 378/156 |
| 5,751,786 A * | 5/1998 | Welters et al. | ................. | 378/156 |
| 5,768,340 A * | 6/1998 | Geittner et al. | ................ | 378/159 |
| 5,778,046 A * | 7/1998 | Molloi et al. | .................. | 378/159 |
| 5,878,111 A | 3/1999 | Schulz | | |
| 5,881,127 A * | 3/1999 | Molloi et al. | .................. | 378/159 |
| 5,966,426 A | 10/1999 | Marra et al. | | |
| 6,061,426 A * | 5/2000 | Linders et al. | ................. | 378/149 |
| 6,118,855 A * | 9/2000 | Welters et al. | ................. | 378/158 |
| 6,181,774 B1 * | 1/2001 | Prins et al. | ..................... | 378/159 |
| 6,188,749 B1 * | 2/2001 | Schiller et al. | ................ | 378/158 |
| 6,198,806 B1 * | 3/2001 | Prins | ............................. | 378/159 |
| 6,226,355 B1 * | 5/2001 | Prins | ............................. | 378/158 |

(Continued)

FOREIGN PATENT DOCUMENTS

| | | |
|---|---|---|
| DE | 19638621 | 2/1998 |
| DE | 69714571 T2 | 4/2003 |
| DE | 10160610 B4 | 1/2004 |

OTHER PUBLICATIONS

German Office Action dated Oct. 17, 2012 for corresponding German Patent Application No. DE 10 2012 207 627.1 with English translation.

*Primary Examiner* — Allen C. Ho
(74) *Attorney, Agent, or Firm* — Lempia Summerfield Katz LLC

(57) ABSTRACT

An adaptive X-ray filter for varying a local intensity of X-ray radiation includes a first chamber containing a magnetorheological or electrorheological first liquid, a second chamber containing a second liquid that absorbs X-ray radiation, and a flexible membrane that separates the first chamber from the second chamber. Using the flexible membrane, a layer thickness ratio of the first liquid and the second liquid may be varied. A heating apparatus that heats the second liquid is arranged in the adaptive X-ray filter. The second liquid is a liquid metal.

15 Claims, 3 Drawing Sheets

(56) References Cited

U.S. PATENT DOCUMENTS

| | | | |
|---|---|---|---|
| 6,252,939 B1 * | 6/2001 | Young et al. | 378/156 |
| 6,269,147 B1 * | 7/2001 | Powell | 378/158 |
| 6,275,568 B1 * | 8/2001 | Prins et al. | 378/158 |
| 6,289,081 B1 * | 9/2001 | Weekamp et al. | 378/156 |
| 6,370,228 B1 * | 4/2002 | Mockler et al. | 378/158 |
| 6,424,698 B1 * | 7/2002 | Weekamp et al. | 378/156 |
| 6,426,999 B2 * | 7/2002 | Prins | 378/156 |
| 6,430,265 B2 * | 8/2002 | Prins et al. | 378/158 |
| 6,438,211 B1 * | 8/2002 | Weekamp et al. | 378/158 |
| 6,440,527 B2 * | 8/2002 | Prins et al. | 428/118 |
| 6,453,012 B2 * | 9/2002 | Herbert | 378/158 |
| 6,453,013 B2 * | 9/2002 | Prins | 378/158 |
| 6,473,492 B2 * | 10/2002 | Prins et al. | 378/158 |
| 6,584,173 B2 * | 6/2003 | Zwart et al. | 378/158 |
| 6,611,578 B2 * | 8/2003 | Snoeren et al. | 378/158 |
| 6,612,166 B2 * | 9/2003 | Golly et al. | 73/170.02 |
| 6,836,535 B2 * | 12/2004 | Toth et al. | 378/159 |
| 7,082,189 B2 * | 7/2006 | Yahata et al. | 378/156 |
| 7,308,073 B2 * | 12/2007 | Tkaczyk et al. | 378/16 |
| 7,652,273 B2 * | 1/2010 | Cernasov | 250/515.1 |

\* cited by examiner

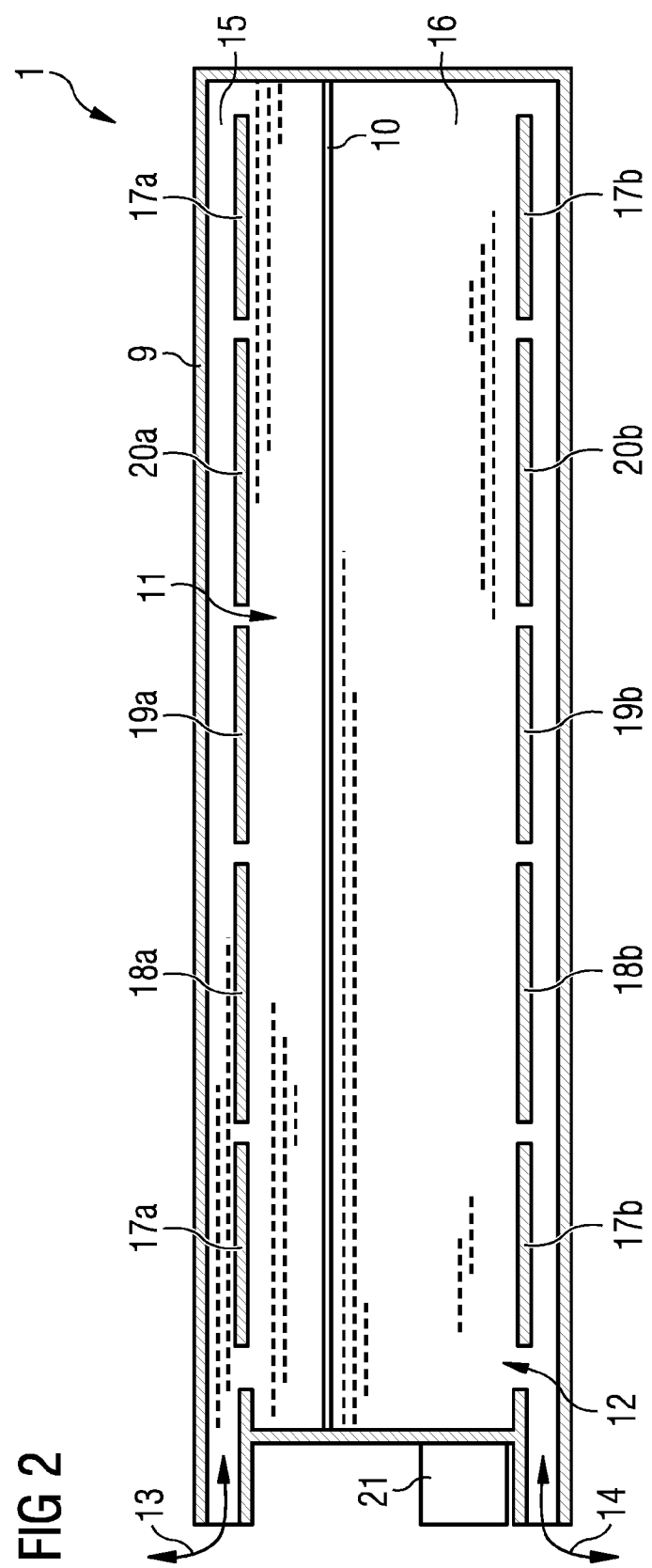

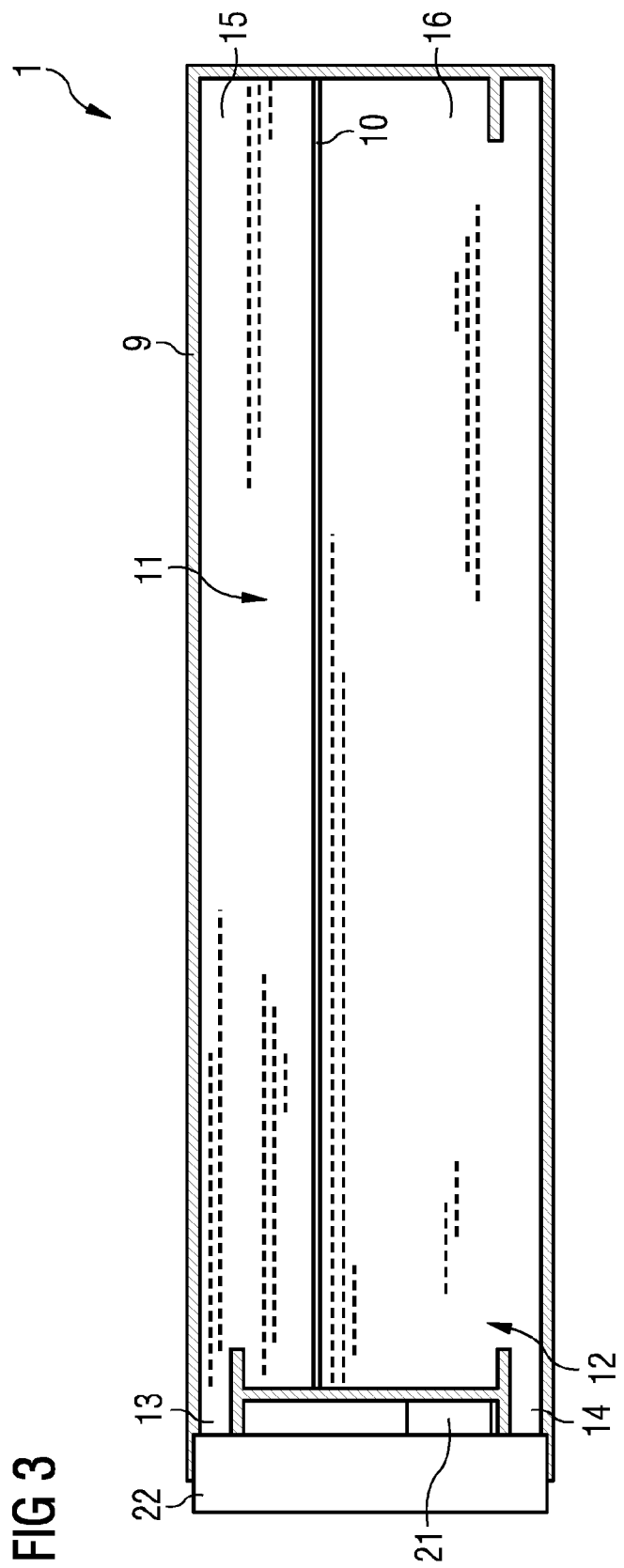

ADAPTIVE X-RAY FILTER

This application claims the benefit of DE 10 2012 207 627.1, filed on May 8, 2012, which is hereby incorporated by reference.

BACKGROUND

The present embodiments relate to an adaptive X-ray filter for varying the local intensity of X-ray radiation.

When examinations are carried out using X-rays, a patient or the patient's organs may exhibit a widely differing absorption behavior in a region under examination with respect to the applied X-ray radiation. For example, in the case of thorax X-rays, the attenuation in the mediastinum (e.g., the region in front of the lobes of the lungs) is very high as a result of the organs located there. In contrast, the attenuation is very low in the region of the lobes of the lungs itself. Both in order to obtain a meaningful X-ray image, and to protect the patient, the applied dose may be set on a region-specific basis such that no more X-ray radiation is delivered than is necessary. In those regions with high attenuation, a greater X-ray radiation dose is to be applied than in regions with lower attenuation. In addition, there are applications in which only one part of the examined region is to be X-rayed with high diagnostic quality (e.g., with less noise). The surrounding parts may be important for orientation but not for the actual diagnostic process. These surrounding regions may therefore be imaged at a lower dose in order to reduce the overall dose applied.

With regard to certain X-ray examinations, variations in the thickness of the human body are compensated for, and thus, the uniformity of the radiation is increased for imaging purposes. This may be achieved by a filter that is designed such that the material thickness thereof may be varied continuously or stepwise in order to thereby enable adjustment of the intensity distribution of the X-ray radiation.

During an X-ray examination skin-damaging soft and medium-soft rays are also produced. The skin-damaging soft and medium-soft rays may have only minor diagnostic relevance because the soft and medium-soft rays are in large part absorbed by the tissue of the patient and do not arrive at the image receptor. For this reason, the radiation is to be "hardened". This provides that the softer rays (e.g., longer wavelength less penetrating rays) are to be filtered out by an X-ray filter.

German patent specification DE 196 38 621 C1 describes a filter that may be adjusted on a region-specific basis for absorbing X-ray radiation. The adjustability is provided by a controllable matrix arranged on a housing for generating a field acting on a liquid contained in the housing. The housing includes at least two chambers that are separated from one another in a sealed manner by a flexible membrane. The chambers contain liquids differing in absorption behavior for X-rays. At least one of the liquids is magnetorheological or electrorheological.

German patent specification DE 101 60 610 B4 discloses a filter for an X-ray examination apparatus for absorbing X-ray radiation having a plurality of controllable elements for generating electrical or magnetic fields that act on a liquid that absorbs X-ray radiation and result in a field-dependent, locally differing absorption behavior via the liquid surface. The form of at least one part of the elements is chosen depending on the form of an object to be examined by the examination apparatus.

SUMMARY AND DESCRIPTION

A disadvantage of the known solutions is the fact that in order to compensate for varying object thicknesses, additional preformed contour diaphragms are to be used. In order to filter out soft radiation components from the applied radiation, special prefilters made of copper or aluminum are used. Contour diaphragms and prefilters are inserted either manually into the accessory rails of the collimator, or are introduced by a costly and space-consuming electrical drive.

The present embodiments may obviate one or more of the drawbacks or limitations in the related art. For example, an adaptive X-ray filter for varying the local intensity of X-ray radiation is provided.

In one embodiment, an adaptive X-ray filter for varying a local intensity of X-ray radiation is provided. The adaptive X-ray filter includes a first chamber containing a magnetorheological or electrorheological first liquid, a second chamber containing a second liquid that absorbs X-ray radiation, and a flexible membrane that separates the first chamber from the second chamber. Using the flexible membrane, a layer thickness ratio of the first liquid and the second liquid may be varied. A heating apparatus that heats the second liquid is arranged in the adaptive X-ray filter. The second liquid may be a liquid metal. A constant fluidity of the liquid metal is provided as a result of heating the liquid metal. Liquid metal exhibits good flow characteristics. Sedimentation may be avoided even after extended periods of nonoperation or in different positions of the adaptive x-ray filter. An alloy such as GALINSTAN, for example, may be used as the liquid metal, which is deemed to be nontoxic and is already employed in applications such as in a thermometer, for example.

In a further embodiment, the adaptive X-ray filter may include a housing in which the first chamber and the second chamber are constructed.

The heating apparatus may include a heating unit that is constructed in the second chamber. For example, a heating unit including a heating coil and a thermostat may be used.

In another embodiment, the adaptive X-ray filter may include an electrode matrix that applies an electrical or magnetic field to the first liquid. Using means, the viscosity of the liquid is varied. This provides that the membrane situated between the first chamber and second chamber is adjusted. By adjusting the membrane, the thickness ratio of the first liquid and the second liquid situated in the two chambers may be set. The local intensity of the X-ray radiation may thus be varied.

In an embodiment, the adaptive filter may include a pump device, by which the ratio of the pressure in at least one chamber may be varied. As a result of setting the pressure, the membrane is specifically adjusted, and the thickness ratio of the first and second liquids contained in the two chambers is thereby varied. The local intensity of the X-ray radiation may thus be varied.

In additional embodiments, the heating unit may include a heating coil and a thermostat.

BRIEF DESCRIPTION OF THE DRAWINGS

FIG. 2 shows a cross-section through one embodiment of an adaptive X-ray filter having an electrode matrix; and FIG. 3 shows a cross-section through one embodiment of an adaptive X-ray filter having a pump unit.

DETAILED DESCRIPTION OF THE DRAWINGS

Figure 1:
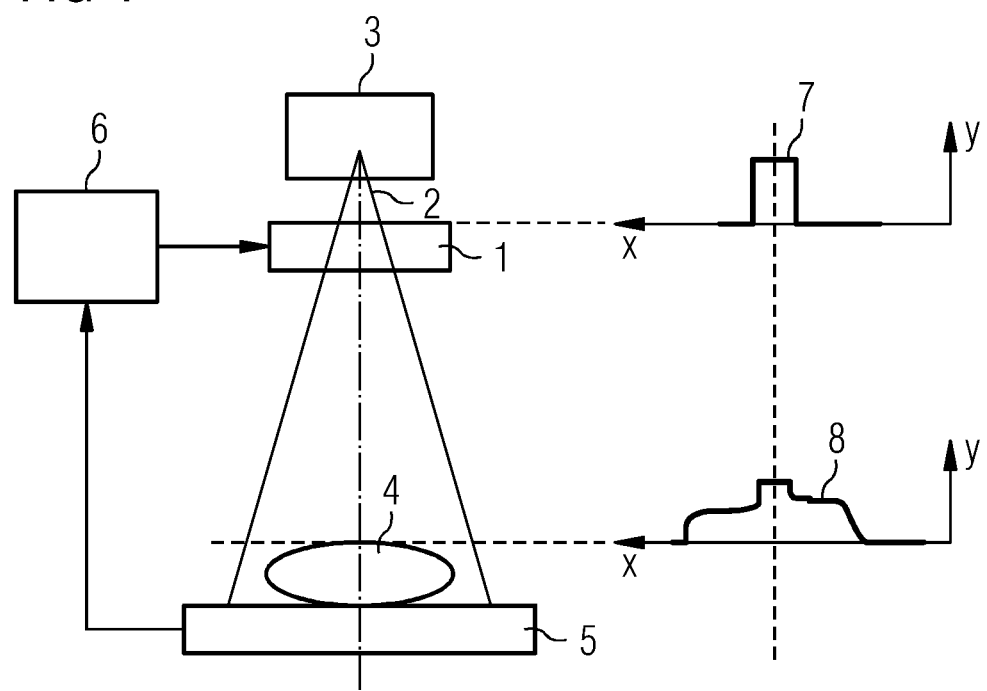
FIG. 1 shows a functional principle of an adaptive X-ray filter.

FIG. 1 shows a functional principle of an adaptive X-ray filter. A location-dependent attenuation of X-ray radiation 2 is effected by an adaptive X-ray filter 1. The X-ray radiation 2 is generated by an X-ray source 3 and penetrates the adaptive X-ray filter 1 and, subsequently, a patient 4. The X-ray radiation 2 is measured by an X-ray detector 5. A control unit 6 controls local attenuation of the X-ray radiation 2 by the adaptive X-ray filter 1.

An intensity profile 7 of the X-ray radiation 2 upstream of the adaptive filter 1 is illustrated schematically at top right in FIG. 1. The intensity y is represented above the axis x, which specifies the location. An almost smooth profile of the intensity y is shown. An intensity profile 8 of the X-ray radiation 2 after passage of the X-ray radiation through the adaptive X-ray filter 1 is illustrated schematically at bottom right in FIG. 1. The variation in the local intensity y caused by the adaptive X-ray filter 1 is shown with the shape of the intensity profile 8.

FIG. 2 shows a cross-section through one embodiment of an adaptive X-ray filter having an electrode matrix. The adaptive X-ray filter 1 includes a housing 9 that is separated by a flexible membrane 10 into a first chamber 11 and a second chamber 12. Each of the chambers 11, 12 has an inlet or outlet 13, 14, via which liquids 15, 16 (e.g., a first liquid 15 and a second liquid 16) contained in the chambers 11, 12 may be delivered or discharged. The first liquid 15 is a magnetorheological liquid or an electrorheological liquid. The second liquid 16 is a liquid metal. An alloy such as GALINSTAN, for example, which is deemed to be nontoxic and is already employed in applications such as in a thermometer, may be used as the liquid metal.

Each inlet or outlet 13, 14 communicates with a reservoir (not shown) for the respective liquid 15, 16 in order to deliver or discharge the liquid 15, 16. A fluid pump (not shown) for applying a minimum pressure to the first liquid 15 contained in the first chamber 11 is provided at least in a line coming off the inlet or outlet the 13. The adaptive X-ray filter 1 may also include a series of upper electrodes 17a, 18a, 19a, 20a that are arranged in the first chamber 11 and a similarly formed series of lower electrodes 17b, 18b, 19b, 20b that are arranged in the second chamber 12, coincident with the upper electrodes 17a, 18a, 19a, 20a. Voltage may be applied separately to the upper electrodes 17a, 18a, 19a, 20a. This provides that an electrical field is established via the respective upper electrodes 17a, 18a, 19a, 20a, to which voltage is applied, and the lower electrodes 17b, 18b, 19b, 20b. The position of the electrical field is determined by the form of the respective upper electrode 17a, 18a, 19a, 20a. The respective upper electrodes 17a, 18a, 19, 20a are spaced apart from one another and isolated from each other. In addition, gaps, through which the respective chamber liquid 15, 16 may circulate, are provided the respective upper electrodes 17a, 18a, 19, 20a. The upper and lower electrodes 17a, 18a, 19a, 20a, 17b, 18b, 19b, 20b together form an electrode matrix.

A heating apparatus 21 that, for example, includes a heating coil (not shown) and a thermostat is arranged in the adaptive X-ray filter 1. The heating coil is not to be situated within an area irradiated by the X-ray radiation 2, as the heating coil would otherwise be imaged on an X-ray produced. The second liquid 16 is heated by the heating apparatus 21. A constant fluidity of the liquid metal 16 is achieved as a result of heating the liquid metal 16. The viscosity of the first liquid 15 is varied by the electrical or magnetic field applied to the first liquid 15. By this, if a corresponding pressure is applied to the second liquid 16 at the same time, the flexible membrane 10 situated between the first and second chambers 11, 12 is adjusted. By adjusting the flexible membrane 10, a thickness ratio of the first liquid 15 and second liquid 16 contained in the two chambers 11, 12 may be set. The local intensity of the X-ray radiation 2 may thus be varied using such an arrangement.

FIG. 3 shows a cross-section through one embodiment of an adaptive X-ray filter 1 having a pump unit. The adaptive X-ray filter 1 includes a housing 9 that is separated by a flexible membrane 10 into a first chamber 11 and a second chamber 12. Each of the chambers 11, 12 has an inlet or outlet 13, 14, via which the liquids 15, 16 contained in the chambers 11, 12 may be delivered or discharged. The first liquid 15 is a liquid that does not absorb X-ray radiation 2. The second liquid 16 is a liquid metal or a colloidal solution including selected chemical elements. The inlets and outlets 13, 14 from or into a reservoir (not shown) are controlled by a pump device 22 having a pressure equalization device (not illustrated) for the respective liquid 15, 16 in order to deliver or discharge the respective liquid 15, 16. The pump device 22 regulates the pressure of the respective liquid 15, 16 at least for one of the two chambers 11, 12. The pump device 22 may also be operable to apply a minimum pressure. A heating apparatus 21 that, for example, includes a heating coil (not shown) and a thermostat is arranged in the adaptive X-ray filter 1. A constant fluidity of the liquid metal 16 is provided as a result of heating the liquid metal 16. As a result of setting the pressure by way of the pump device 22 in at least one of the two chambers 11, 12, the flexible membrane 10 is specifically adjusted, and the thickness ratio of the first and second liquids 15, 16 contained in the two chambers 11, 12 is thereby varied. Varying the thickness ratio of the first and second liquids 15, 16 contained in the two chambers 11, 12 allows the local intensity of the X-ray radiation 2 or an X-ray radiation characteristic (e.g., filtering out soft radiation) may be varied. The thickness ratio of the liquids 15 and 16 may be captured by the pump device 22 having the pressure equalization device (not shown).

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An adaptive X-ray filter for varying a local intensity of X-ray radiation, the adaptive X-ray filter comprising:
   a first chamber comprising a first liquid;
   a second chamber comprising a second liquid, wherein the second liquid is a liquid metal and is operable to absorb X-ray radiation;
   a flexible membrane operable to separate the first chamber from the second chamber, and operable to vary a layer thickness ratio of the first liquid and the second liquid; and
   a heating apparatus operable to heat the second liquid.

2. The adaptive X-ray filter of claim 1, wherein the first liquid is a magnetorheological fluid.

3. The adaptive X-ray filter of claim 1, wherein the first liquid is an electrorheological fluid.

4. The adaptive X-ray filter of claim 1, further comprising a housing, in which the first chamber and the second chamber are constructed.

5. The adaptive X-ray filter of claim 4, wherein the heating apparatus comprises a heating unit adjacent to the second chamber.

6. The adaptive X-ray filter of claim 5, further comprising an electrode matrix operable to apply an electrical field or a magnetic field to the first liquid.

7. The adaptive X-ray filter of claim 5, further comprising a pump device operable to vary a ratio of the pressure in the first chamber, the second chamber, or the first chamber and the second chamber.

8. The adaptive X-ray filter as claimed in claim 5, wherein the heating unit comprises a heating coil and a thermostat.

9. The adaptive X-ray filter of claim 4, further comprising an electrode matrix operable to apply an electrical field or a magnetic field to the first liquid.

10. The adaptive X-ray filter of claim 4, further comprising a pump device operable to vary a ratio of the pressure in the first chamber, the second chamber, or the first chamber and the second chamber.

11. The adaptive X-ray filter of claim 1, further comprising an electrode matrix operable to apply an electrical field or a magnetic field to the first liquid.

12. The adaptive X-ray filter as claimed in claim 11, wherein the heating unit comprises a heating coil and a thermostat.

13. The adaptive X-ray filter of claim 1, further comprising a pump device operable to vary a ratio of the pressure in the first chamber, the second chamber, or the first chamber and the second chamber.

14. The adaptive X-ray filter as claimed in claim 13, wherein the heating unit comprises a heating coil and a thermostat.

15. The adaptive X-ray filter of claim 1, wherein the second fluid comprises a colloidal solution.

* * * * *